United States Patent [19]
Kroll

[11] Patent Number: 5,527,346
[45] Date of Patent: Jun. 18, 1996

[54] IMPLANTABLE CARDIOVERTER DEFIBRILLATOR EMPLOYING POLYMER THIN FILM CAPACITORS

[75] Inventor: Mark W. Kroll, Minnetonka, Minn.

[73] Assignee: Angeion Corporation, Plymouth, Minn.

[21] Appl. No.: 342,637

[22] Filed: Nov. 21, 1994

Related U.S. Application Data

[63] Continuation of Ser. No. 166,212, Dec. 13, 1993, abandoned.

[51] Int. Cl.⁶ ......................................... A61N 1/39
[52] U.S. Cl. ............................................... 607/5
[58] Field of Search .................................. 607/4, 5

[56] References Cited

U.S. PATENT DOCUMENTS

| | | | |
|---|---|---|---|
| 3,614,954 | 10/1971 | Mirowski et al. | |
| 4,945,449 | 7/1990 | Cansell et al. | 361/273 |
| 5,337,209 | 8/1994 | Sutherland et al. | 361/321.5 |
| 5,342,399 | 8/1994 | Kroll | 607/5 |
| 5,384,544 | 1/1995 | Flugstad et al. | 324/678 |

FOREIGN PATENT DOCUMENTS 9320892  10/1993  WIPO ..................... 607/5

OTHER PUBLICATIONS

Alterations Inudced By A Singe Defibrillation Shock Appiled Through A Chronically Implanted Catheter Electrode By Barker-Voelz et al., J. Electrocardiology 16(2):167–180, 1983.

*Primary Examiner*—William E. Kamm
*Assistant Examiner*—Kennedy J. Schaetzle
*Attorney, Agent, or Firm*—Patterson & Keough

[57] ABSTRACT

An implantable cardioverter defibrillator (ICD) system employs polymer film capacitor technology for the capacitor system. Unlike existing ICD systems which utilize electrolytic capacitors, the ICD system of the present invention utilizes polymer thin film capacitors to deliver an electrical countershock having an effective pulse duration of greater than the chronaxie duration of the human heart from a maximum stored energy of less than about 35 joules when charged to a maximum charging voltage of at least about 800 volts. Preferably, the polymer thin film capacitors having a dielectric thickness of between about 1,000 nm and 10,000 nm and an effective capacitance of the less than about 80 μF with a maximum charging voltage of less than about 1500 volts or a maximum peak current of less than about 30 amperes.

9 Claims, 7 Drawing Sheets

— INITIAL VOLTAGE REQUIRED FOR A FINAL VOLTAGE OF 200
--- INITIAL VOLTAGE REQUIRED FOR A FINAL VOLTAGE OF 250

IMPLANTABLE CARDIOVERTER DEFIBRILLATOR EMPLOYING POLYMER THIN FILM CAPACITORS

RELATED APPLICATIONS

This application is an FWC of Ser. No. 08/166,212, filed Dec. 13, 1993, now abandoned.

This application is related to an application filed in the United States Patent and Trademark Office concurrently with the present application and entitled METHOD AND APPARATUS FOR UTILIZING SHORT TAU CAPACITORS IN AN IMPLANTABLE CARDIOVERTER DEFIBRILLATOR, Ser. No. 08/166,216, now U.S. Pat. No. 5,391,186, which is assigned to the assignee of the present invention, a copy of which is attached hereto and the disclosure of which is hereby incorporated by reference in the present application. This application is also related to two application previously filed in the United States Patent and Trademark Office, the first of which is entitled CURRENT TRUNCATED WAVEFORM DEFIBRILLATOR, Ser. No. 08/096,009, filed on Jul. 22, 1993, now U.S. Pat. No. 5,413,591, and the second of which is entitled IMPLANTABLE CARDIOVERTER DEFIBRILLATOR HAVING A SMALLER DISPLACEMENT VOLUME, Ser. No. 08/033,632, filed on Mar. 15, 1993, both of which are assigned to the assignee of the present invention, a copy of each of which is attached hereto and the disclosure of which is hereby incorporated by reference.

BACKGROUND

1. Field of the Invention

The present invention relates generally to implantable cardioverter defibrillators and, more specifically, to an implantable cardioverter defibrillator employing polymer thin film capacitors.

2. Background of the Invention

The incidence of heart disease in the United States is significant with approximately one out of every two deaths is attributable to heart disease. One of the leading complications secondary to heart disease is cardiac arrythmia resulting in sudden cardiac death. Because of the high prevalence of sudden cardiac death due to cardiac arrythmia there is a demonstrated need for an implantable cardioverter defibrillator (ICD) system. To be useful, an ICD systems must be self-contained, complete, and capable of effective repetitious function autonomous from the outside world. A direct corollary of these requirements is that the system be small enough to be implanted. The size limitations imposed by an implantable device generally have prevented the technology and techniques applicable to external defibrillator systems from being applied to ICD systems. Even with the development of novel technology and techniques for generating defibrillation pulses or countershocks in an implantable device, present day ICD systems are still sufficiently large so as to require implantation within the abdomen or abdominal wall of a patient.

A more ideal size for an ICD system would be the size that implantable cardiac pacemakers have achieved, such that the device is capable of being implanted in the subcutaneous space just inferior to either clavicle. Unfortunately, pacemakers are capable of smaller sizes quite simply because their power requirements are significantly less than the power requirements of ICD systems. While pacemakers have energy output requirements that are in the microjoule output range, ICD systems, to be effective, must be capable of delivering repeated defibrillation countershocks above at least about 15 joules for each countershock. In order to achieve such high energy outputs, existing ICD systems have utilized larger batteries, as well as large high voltage capacitors to generate the required high energy defibrillation countershock. Consequently, one of the major challenges in reducing the size of an ICD system is how to decrease the effective size limits of both the batteries and capacitors that are used by the ICD system.

Presently, there are three different types of ICD systems which have received device approval from the Federal Drug Administration, the PCD™ device, available from Medtronic, Inc., of Minneapolis, Minn., the Cadence® device, available from Ventritex, Inc., of Mountain View, Calif., and the Ventak-P® device, available from Cardiac Pacemakers, Inc., of St. Paul, Minn. The primary components of all existing ICD systems include an automatic monitoring and detection mechanism, a capacitor system, a battery system and control circuitry for detecting a ventricular arrhythmia and controlling delivery of a high-voltage capacitive-discharge electrical countershock in response by charging and then discharging the capacitor system. To achieve successful defibrillation, the ICD system must deliver a high voltage electrical countershock with an initial voltage of greater than about 500 to 600 volts.

The existing ICD systems are all capable of delivering a maximum countershock of up to 700 to 750 volts having a total energy of between 31 to 44 joules. At the time an ICD system is implanted in a patient, the attending physician will empirically determine a minimum defibrillation threshold for the patient, and will program the charging voltages for the countershocks to be delivered as part of a therapy regimen within the range of maximum voltages allowed by the device. In addition, the attending physician can also typically program when the electrical countershock is to be truncated by programming the duration of the countershock in a range from about 6 to 9 milliseconds. Alternatively, the duration can be altered by programming the initial discharge voltage of the ICD system and allowing the tilt of the ICD system to establish the point at which the countershock will be truncated. The tilt of an ICD system is defined as the percentage decline in the output voltage from the charging voltage to the voltage at the time the discharge is truncated. For existing ICD systems, the tilt is typically set at about 65%.

The capacitor system is a critical element of the ICD system, both in terms of how effective the ICD system can be and how small it can be. By definition, a capacitor is comprised of two conductive surfaces separated by an insulating material. The insulating material is known as the "dielectric" of the capacitor. When the two surfaces of the capacitor are oppositely charged by a voltage source, such as the battery in an ICD system, electrical energy is effectively stored by the capacitor in the polarized dielectric. The capability of a capacitor to store electrical charge is the capacitance value of the capacitor. For a given dielectric material, the thinner the dielectric, the higher the capacitance value. A thinner dielectric also decreases the overall size of the capacitor. Unfortunately, there are limits as to how thin a dielectric can be due to the fact that very thin dielectrics will break down under high voltages as there is simply an insufficient amount of insulating material between the conductive surfaces to withstand the high voltages.

When all of these requirements for an ICD system are considered, the aluminum oxide electrolytic capacitor has proven to be the best capacitor technology for use in ICD systems to date, and is presently used in all existing ICD systems. The aluminum oxide dielectric can be made very thin because the dielectric oxide is essentially grown on the conductive surface of a very thin sheet of aluminum that has been etched to increase its effective surface area. As a result, aluminum oxide electrolytic capacitors have higher energy densities (typically 1.7 to 1.8 joules/cc) than other types of capacitor technologies (typically much less than 1.5 joules/cc). Due to the nature of the aluminum oxide dielectric, however, electrolytic capacitors are limited to maximum rated charging voltages in the range of approximately 350 to 375 volts. Beyond 375 volts, electrolytic capacitors begin to suffer from significant leakage current across the dielectric. This leakage current increases rapidly as the voltage is increased and charging of the electrolytic capacitor will cease when the leakage current equals the charge current. As a result, the existing ICD systems all utilize two electrolytic capacitors in series, each being charged to approximately 350 to 375 volts, which are then discharged to deliver the high voltage shock to the myocardium having a maximum voltage of approximately 700 to 750 volts.

Although electrolytic capacitors are used in existing ICD systems in order to take advantage of their excellent capacitance to volume ratio, electrolytic capacitors suffer from several major drawbacks. First, the useful charging voltage for electrolytic capacitors is limited to approximately 350 to 375 volts due to the current leakage effects encountered at higher charging voltages. Electrolytic capacitors, due to the nature of the oxide dielectric, begin to break down and suffer from significant current leakage with charging voltages over 375 volts. Because and ICD system needs to produce an initial discharge voltage of at least about 600 volts, this drawback requires that two electrolytic capacitor be used in series in order to generate the required initial discharge voltage, thus increasing the number of components within the ICD system and, to a certain extent, complicating the electronic design of the ICD system.

Another significant disadvantage of electrolytic capacitors is the degradation of the oxide dielectric over time. The oxide can be reformed by periodic charging to full voltage. On a monthly or quarterly basis, the capacitor system will need to be charged to its full voltage. In early ICD systems, this requirement necessitated the patient's periodic return to the hospital to accomplish the reforming of the capacitor system. Later ICD systems have used automatic reforming of the electrolytic capacitors from the internal battery system on a periodic basis, but this practice is wasteful of valuable energy in an ICD system that only has a finite and depletable source of power.

Still another drawback of electrolytic capacitors is that a substantial portion of the energy density advantage over other capacitor technologies is lost to packaging inefficiencies within the ICD system as a result of the cylindrical packaging shape that is required of electrolytic capacitors. When the lost volume of fitting a cylindrical volume into a rectangular volume is factored into the energy density calculations, the energy density for electrolytic capacitors is effectively only about 1.3 to 1.4 joules/cc.

At least one other capacitor arrangement has been proposed for use in an ICD system. In U.S. Pat. No. 3,614,954 issued to Mirowski, the device described charges a capacitor of an unspecified capacitor technology to a charging voltage of 2,500 volts in order to generate approximately 50 joules of energy for the electrical countershock. At the time the Mirowski patent application was filed, the available capacitor technologies that had breakdown voltages of greater than 2,500 volts were probably mica or oil-soaked paper dielectric capacitors. For a number of reasons, and regardless of the capacitor technology utilized, the capacitor arrangement suggested by Mirowski would not be suitable for use in a practical ICD system, and, in fact, no ICD system has ever been developed using a capacitor charged to such a high voltage. The primary reasons for this are the unacceptably high peak currents that would be generated by an electrical countershock of such a high voltage, the excessively high voltages which prevent use of transistor switches and the large size of the capacitor and battery system required to charge and store 50 joules of energy.

With respect to the first reason, myocardial tissue resistance between any two implanted discharge electrodes has been found to be about 50 ohms ($\Omega$) on average. This value of 50 ohms has become the accepted average resistance of the myocardial tissue between the discharge electrodes for ICD systems. Using this average resistance value, the peak current of an electrical countershock delivered from a capacitor charged to 2500 volts would be 2500 volts/50 ohms, or 50 amperes. It is known that peak currents in excess of about 30 amperes during delivery of an electrical countershock can lead to tissue destruction in the heart in a zone beginning from the center of the electrical field and extending outward. High peak currents also stun tissue extending radially outward from the border of the destruction zone for some additional distance. For additional background on this type of high current tissue destruction, reference is made to: "Alterations Induced by a Single Defibrillation Shock Applied through a Chronically Implanted Catheter Electrode" by Barker-Voelz et al. in *J. Electrocardiology* 16(2): 167–180, 1983.

With respect to the second reason, most microelectronic switching circuitry have maximum switching voltages of less than about 1000 volts. Certain types of microelectronic switching circuitry, such as silicon controlled rectifiers or certain high power MOSFET transistors are capable of handling switching voltages of up to about 2000 volts. To date, however, no microelectronic switching circuits have been developed which could handle the 2500 volts required by the Mirowski device. Thus, the Mirowski device requires the use of individual high power switching transistors, devices which occupy significantly more space in the device than microelectronic switching circuitry.

As for the third reason, an analysis of just the stored energy requirements of the Mirowski device and existing ICD systems reveals that the Mirowski device, which stores 50 joules of energy, would require a battery and capacitor system that are at least 15% to 40% larger than the battery and capacitor systems of existing ICD systems, which store maximum energies of between about 31 to 44 joules. While it might seem possible to lower the maximum stored energy of the Mirowski device to that of existing ICD systems, the maximum stored energy requirements of the Mirowski device effectively cannot be lowered because to do so would decrease the overall duration of the defibrillation countershock below about 2 milliseconds, a point below which defibrillation effectiveness decreases significantly. Thus, it is not practical to decrease the size of the Mirowski device by decreasing the stored energy requirements below the 50 joules taught in the Mirowski patent.

A potential alternative capacitor technology to electrolytic capacitors is the polymer thin film capacitor. In a polymer thin film capacitor, the dielectric is a very thin polymer film that is formed mechanically through high precision rolling operations. Conductive layers of aluminum are then deposited on each surface of the polymer film. The advantages of the polymer thin film capacitors are that they have very high breakdown voltages and very good charge retention. As a result, if a polymer thin film capacitor were used in an ICD system, there would be no need to use two separate capacitors to achieve the initial discharge voltage required for defibrillation. Nor would there be a need to reform the capacitor due to a break down of the dielectric.

To date, however, polymer thin film capacitors have not been suggested for use in an ICD system for several reasons due to the nature of the polymer thin film dielectric. First, polymer thin film capacitors have lower average energy densities than electrolytic capacitors because the polymer thin film dielectric is substantially thicker than the aluminum oxide dielectric. Second, polymer thin film capacitors operate more efficiently at higher voltages and, hence, the energy density in the voltage range of 700 to 750 volts, for example, is even less efficient.

Although a single polymer thin film capacitor can withstand significantly higher voltages than an electrolytic capacitor, polymer thin film capacitors constructed to work in the 700 to 750 volt range and capable of storing 35 to 40 joules of energy will occupy substantially more volume than the two aluminum oxide electrolytic capacitors presently used in existing ICD systems. This size factor is directly related to how thinly the polymer film dielectric can be rolled. Aluminum oxide dielectric is approximately 1.5 nanometers (nm) thick per rated charge volt. Therefore, an electrolytic capacitor rated at 350 volts will have a dielectric thickness of approximately 525 nm. In contrast, polymer thin films simply cannot be rolled any thinner than about 1,000 nm due to the fact that pin hole defects and impurity domains capable of causing catastrophic breakdown within the polymer thin film dielectric increase dramatically at thicknesses below about 1,000 nm. In practice, most manufacturers of polymer thin film capacitor stay nearer to the 10,000 nm thickness range for the polymer thin film dielectric in order to avoid catastrophic breakdown secondary to pin hole defects and impurity domains. Because the capacitance value of a capacitor is a function of the thickness between the conductive surfaces, a polymer thin film capacitor will have to have at least twice the surface area of an electrolytic capacitor in order to compensate for being at least twice as thick. Consequently, a polymer thin film capacitor would need to be at least twice the volume of its electrolytic counterpart. This is hardly an ideal situation for use in an ICD system, and, as a result, polymer thin film capacitors have not been suggested for use in ICD systems because of the comparatively enormous sizes required.

While the use of electrolytic capacitor for ICD systems has allowed for the creation of practical implantable devices that can deliver effective electrical countershocks, there are inherent limitations of electrolytic capacitors which hinder any further reduction in the size of ICD systems by reducing the size of the capacitor system necessary to deliver the capacitive-discharge electrical countershock. Unfortunately, none of the other capacitor technologies appear to offer a more practical alternative to the use of electrolytic capacitors for ICD systems. Therefore it would be desirable to provide an implantable cardioverter defibrillator system which could employ the use of a capacitor technology other than electrolytic capacitors. In addition, it would be advantageous to provide an implantable cardioverter defibrillator system that could take advantage of the higher charging voltages available with polymer thin film capacitors.

SUMMARY OF THE INVENTION

The present invention is an implantable cardioverter defibrillator (ICD) system that employs polymer film capacitor technology for the capacitor system. Unlike existing ICD systems which utilize electrolytic capacitors, the ICD system of the present invention utilizes polymer thin film capacitors to deliver an electrical countershock having an effective pulse duration of greater than the chronaxie duration of the human heart and having a maximum peak current of less than about 30 amperes from a maximum stored energy of less than about 35 joules when charged to a maximum charging voltage of at least about 800 volts.

In one embodiment, a polymer thin film capacitor having an effective capacitance of less than about 80 µF is charged to between about 800 to 1500 volts to generate a maximum stored energy of up to about 35 joules. The stored energy in the polymer thin film capacitor is discharged in such a way that the effective duration of the discharge is extended beyond about 3 milliseconds. In this way, the effectiveness of a high voltage countershock is not compromised by a pulse duration that is too short to result in successful defibrillation. In addition, because the effective capacitance required by the present invention is only about one-half that of existing ICD systems, the overall size of the polymer thin film capacitor is reduced in comparison to the size of the electrolytic capacitors used in existing ICD systems.

In another embodiment, a polymer thin film capacitor having an effective capacitance of less than about 30 to 35 µF is charged to a charging voltage of greater than about 1250 to 1500 volts to store a maximum energy of up to about 35 joules and a current truncation system that is capable of non-linear current truncation is electrically connected in series with the discharge electrodes to prevent the peak current of the electrical countershock from exceeding about 25 to 30 amperes. Depending upon the capacitance value and the charging voltage, the stored energy in the polymer thin film capacitor is discharged in such a way that the effective duration of the discharge is extended beyond about 3 milliseconds.

In essence, the present invention can make use of polymer thin film capacitor technology by recognizing that, in order to achieve the energy storage density necessary for an ICD system, polymer thin film capacitors must have smaller effective capacitance values than the capacitor systems used in existing ICD systems and must be operated at higher voltages than existing ICD systems. With the smaller effective capacitance values, however, the effective discharge duration of a truncated electrical countershock can easily fall below the chronaxie duration of the human heart, about 2 to 4 milliseconds, below which the effectiveness of the electrical countershock is significantly decreased. If the electrical countershock is not truncated, it can produce detrimental trailing voltages or if the initial voltage is too high, it can produce detrimental peak currents. Therefore, in one embodiment the present invention provides circuitry to interrupt the capacitive-discharge so as to extend the duration of the discharge to at least about 3 milliseconds, for example. In addition, another embodiment of the present invention insures that the peak current generated by using discharge voltages in excess of those used by existing ICD systems will not cause damage to the myocardial tissue. To this end, when signficiantly higher intial voltages are used to prevent low trailing voltages from occuring in the electrical countershock, the present invention provides for non-linear current limiting circuitry to effectively limit the peak current to less than about 30 amperes.

The reason why it is necessary to operate polymer thin film capacitors at voltages higher than those used in existing ICD systems is due to the fact that, unlike electrolytic capacitors with an oxide dielectric, the maximum electrical field that can be sustained across a polymer film dielectric is not achievable at relatively low voltage, e.g., voltages less than about 5,000 to 10,000 volts depending upon the specific dielectric material. Below what will be referred to as a minimum effective field voltage for the particular capacitor, the maximum electrical field cannot be applied across the conductive surfaces of the capacitor. As a result, the energy density at lower voltage is significantly less than the theoretical energy density attainable at voltages greater than or equal to the minimum effective field voltage. This decreased energy density, in turn, means that the polymer thin film capacitors are much larger than equivalent electrolytic capacitor systems at the relatively high capacitance values (140 µF and above) and relatively low charging voltages (750 volts and below) where existing ICD systems operate.

For polymer thin film capacitors, the minimum effective field voltage is determined by the thickness of the polymer film. For very thin films below 10,000 nm, the existence of defects and impurities essentially causes breakdowns at field voltages that are less than the minimum effective field voltage. These breakdowns are typically not a problem in those situations where very high voltages are used, or where the overall volume of the capacitor is not a concern. For ICD systems, however, these problems have effectively prevented polymer thin film capacitors from being used in the past. To compensate for these problems, the present invention recognizes that the net effect of lower breakdown voltages due to the existence of defects and impurities in thin films is that, for thin films of less than 10,000 nm and at voltages below the minimum effective field voltage, the maximum electrical field is proportional to the dielectric thickness. Instead of using a linear relationship between charging voltage and film thickness, the present invention approximates the relationship between the maximum charging voltage as a function of the square of the thickness of the polymer film for thin films of thicknesses between about 1,000 to 10,000 nm. Using this relationship, it is possible to optimize the capacitance value and charging voltage of the ICD system so as to achieve the highest possible energy density for the polymer thin film capacitor system.

DETAILED DESCRIPTION OF THE DRAWINGS

DETAILED DESCRIPTION OF THE PREFERRED EMBODIMENT

Figure 1:
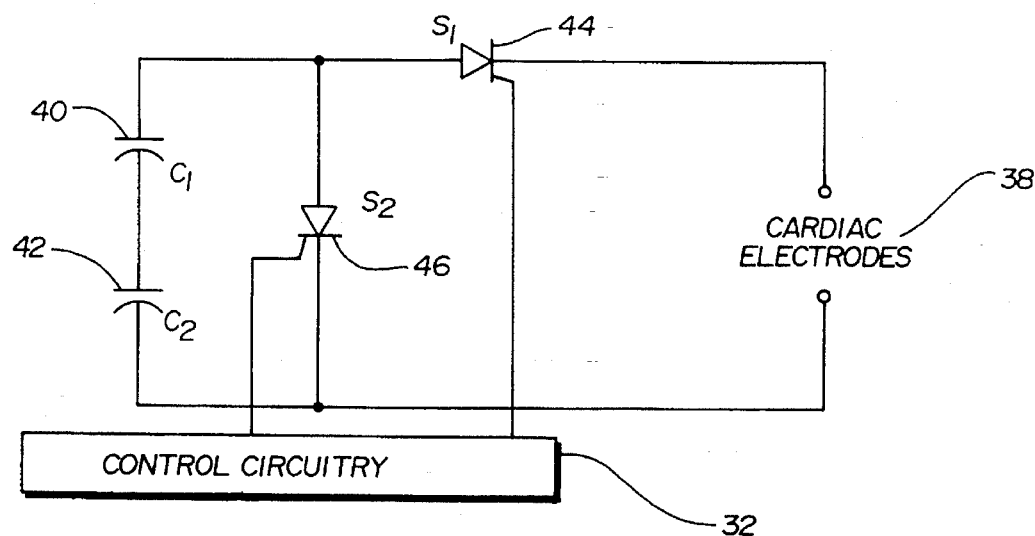
FIG. 1 is a simplified electrical schematic diagram of the original Schuder circuit for an existing ICD system.

FIG. 1 depicts a simplified diagrammatic representation of the discharge circuit for an existing implantable cardioverter defibrillator (ICD) system. High voltage capacitors 40 and 42 represent the dual electrolytic high voltage capacitors whereby capacitors 40 and 42 are each charged to approximately 375 volts. Once fully charged, capacitors 40 and 42 are discharged in series through silicon controlled rectifier (SCR) 44 as the activating switch delivering the countershock to the myocardium via countershock electrodes 38. In the original Schuder circuit the countershock discharge was truncated through activation of a second SCR 46 which starves SCR 44 by shorting capacitors 40 and 42. Control circuitry 32 responds to a sensing signal (not shown) to detect the presence of a cardiac arrhythmia, and, in response, selectively controls the charging and discharging of capacitors 40 and 42. The circuit depicted in FIG. 1 is inefficient by wasting the leftover energy when terminating the defibrillation countershock in this fashion.

Figure 2:
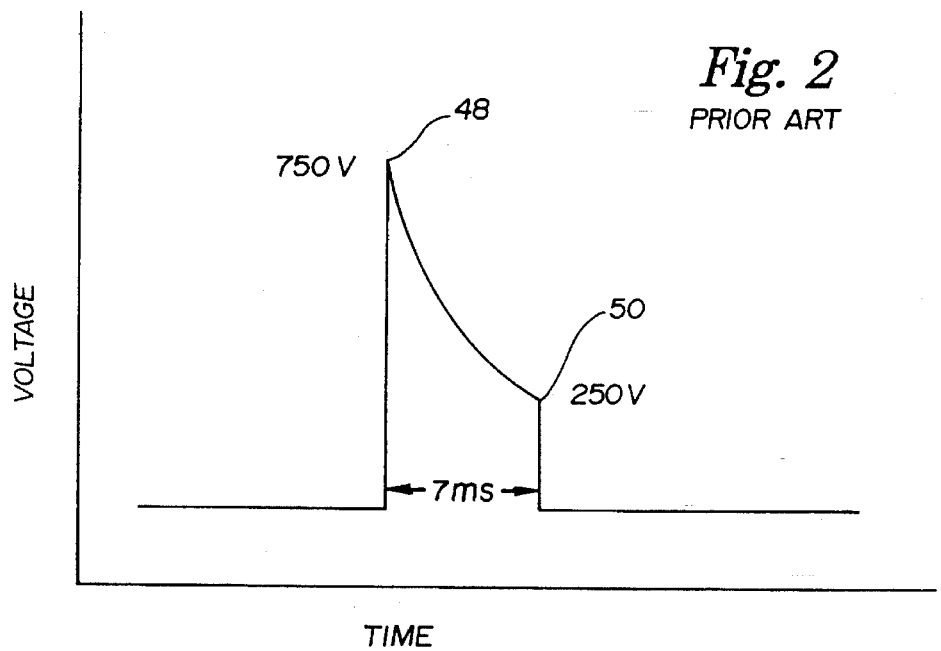
FIG. 2 is a graph depicting the voltage discharge for a typical monophasic discharge pulse generated by the circuit shown in FIG. 1.
Figure 3:
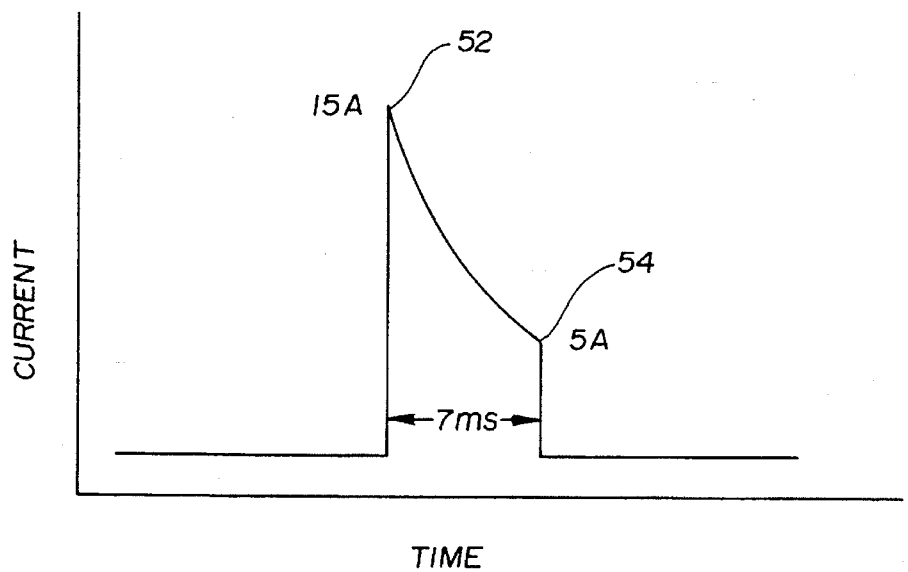
FIG. 3 is a graph depicting the current output of a monophasic pulse as shown in FIG. 2.

FIG. 2 shows a graphic representation of the voltage versus time plot of a single monophasic discharge of the Schuder circuit of FIG. 1. As shown at time point 48 there is an initial peak voltage of 750 volts to capacitors 40 and 42 that exponentially decays according to the time constant for capacitors 40 and 42 through the resistance of the myocardium. The average resistance of the myocardium across internally placed discharge electrodes averages 50 ohms. This provides a time constant of approximately 7 milliseconds for an equivalent ICD system capacitance of 140 µF, as is typical for capacitors 40 and 42 when connected in series. Truncation of the capacitive discharge at the time constant results in roughly 250 volts at time point 50 across the discharge electrodes when the defibrillating discharge is truncated by closing SCR 46 to starve SCR 44. After time point 50, the capacitor charge is shunted through SCR 46 truncating the curve as seen in FIG. 2. FIG. 3 depicts the current seen at the cardiac electrodes and corresponds to the voltage discharge depicted in FIG. 2. Peak current flow 52 represents the initial peak current and is seen to decay in an exponential fashion to current flow 54 at time of truncation some 7 millisecond later. The terminal current is about 5 amperes at time of truncation.

Figure 4:
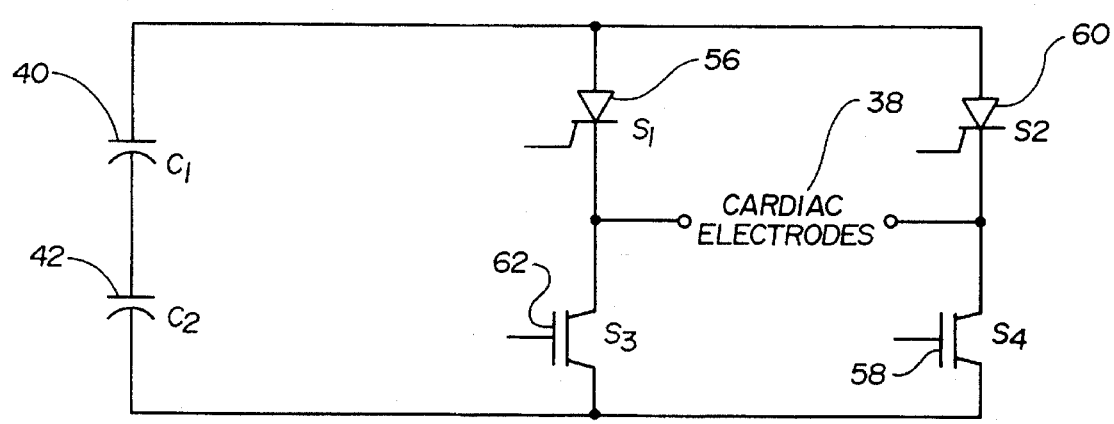
FIG. 4 is a simplified electrical schematic of an ICD using an H bridge output circuit to the discharge electrodes in an existing ICD system.

Numerous studies on the electrophysiology of defibrillation have revealed that a fibrillating myocardium is more responsive to what is now termed a biphasic countershock discharge. This is in contrast to the Schuder circuit of FIG. 1 which produces a monophasic countershock discharge as depicted in FIG. 2. FIG. 4 represents a simplistic circuit depiction of a bridge circuit using solid state switches to give rise to an H-bridge configuration allowing for reversal of polarity at the cardiac electrodes. As with FIG. 1, control circuitry 32 responds to a sensing signal (not shown) to detect the presence of a cardiac arrhythmia, and, in response, selectively controls the charging and discharging of capacitors 40 and 42. As shown in FIG. 4, high voltage electrolytic capacitors 40 and 42 are each charged to approximately 375 volts. A biphasic defibrillation countershock is initiated by closing SCR 56 and metal oxide semiconductor field effect transistor (MOSFET) 58. After a predetermined period of time of discharge across cardiac electrodes 38, MOSFET 58 is opened which starves the current across SCR 56 turning it off as well. The defibrillation countershock is completed by then closing SCR 60 and MOSFET 62 effectively reversing the polarity across cardiac electrodes 38. The countershock is truncated by opening MOSFET 62 which also in effect starves the current across SCR 60 allowing it to open as well.

Figure 5:
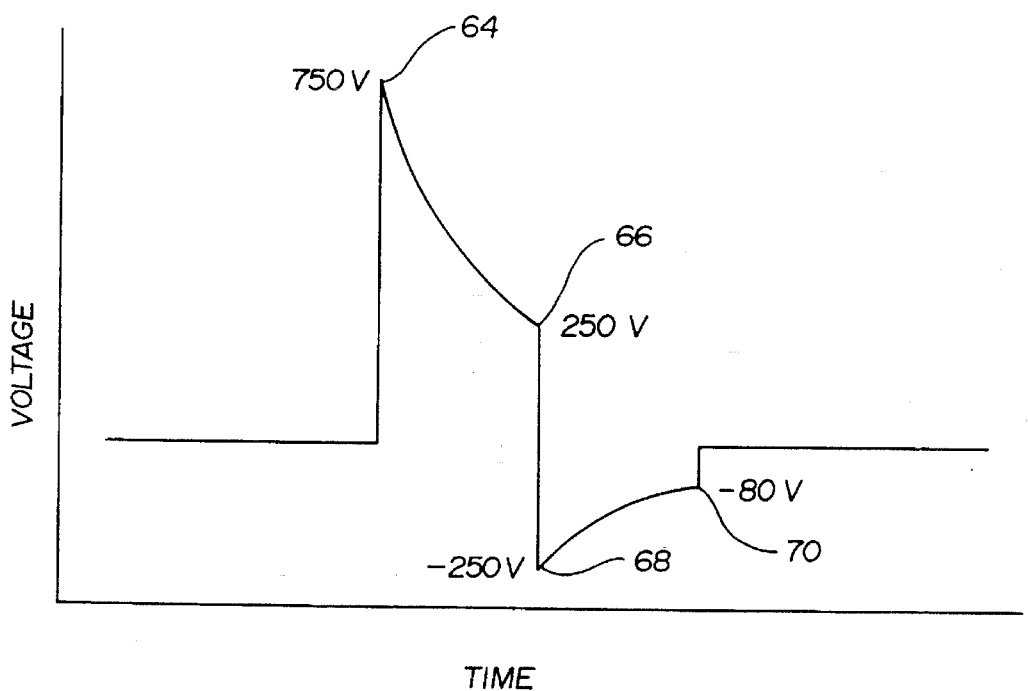
FIG. 5 is a graph depicting the voltage discharge for a typical biphasic countershock pulse generated by the circuit shown in FIG. 4.

FIG. 5 is a voltage versus time graph depicting the biphasic discharge as seen at the cardiac electrodes. Peak initial voltage point 64 corresponds to the initial orientation of the voltage discharge cross cardiac electrodes 38. The second time period approximately 7 milliseconds later demonstrates the truncation of the initial form of the countershock at point 66. With closure of SCR 60 and MOSFET 62 the voltage across electrodes is reversed to point 68 which then exponentially decays to point 70 when the countershock discharge is truncated by opening MOSFET 62 and SCR 60.

FIG. 1 and FIG. 4 represent the classical circuit designs for conventional ICD systems. In general, and for reference throughout this application, cardiac electrode polarity and phase will be understood by reference to a discharge control circuit which may include either of the classic circuit configurations, but is not intended to be limited to them.

Aluminum oxide electrolytic capacitors of the type used in existing ICD systems for capacitors 40 and 42 are capable of storing approximately 1.77 joules per cc of volume. This energy density is predicated on the electrolytic capacitor having a cylindrical shape. As is common, electrolytic capacitors are generally mounted within the body of the ICD system in a generally rectangular space. When the inefficiencies of putting a cylindrical shape in a generally rectangular space are taken into account, the effective energy density value decreases to about 1.33 joules/cc for aluminum oxide electrolytic capacitors as used within an ICD system. A derivation of these values is helpful in understanding the how the present invention can make use of polymer thin film capacitors in place of aluminum oxide electrolytic capacitors.

Generally, capacitance is given by the following equation:

$$C = K * \epsilon * (A/t) \qquad \text{Eq. (1)}$$

where C is capacitance, K is the dielectric constant, $\epsilon$ is the permitivity constant for free space, A is the surface area of the facing electrodes, and t is the thickness of the dielectric as defined by the distance between the electrode surfaces of the capacitor. The other equation which is usually helpful in defining the energy density of a capacitor defines a linear relationship between the charging voltage, V, and the maximum electrical field, $F_m$, as a function of the thickness t of the dielectric:

$$V = F_m * t \qquad \text{Eq. (2)}$$

The capacitance can also be defined by reworking the standard equation for the energy of a capacitive discharge:

$$E = 0.5 * C * V^2 \qquad \text{Eq. (3)}$$

where E is the energy in joules and V is the charging voltage applied to the capacitor.

Because the maximum charging voltage V is effectively fixed at about 750 volts for a pair of electrolytic capacitors, the solution to Eq. (3) for a given ICD system has been a straight forward matter of selecting the optimum capacitance value for a given desired stored energy E, which is selected by presently accepted medical convention as the minimum threshold energy required to achieve successful defibrillation multiplied by a safety factor of 2, or having an additional 10 joules of energy as a safety factor. For a monophasic countershock, for example, the accepted minimum threshold energy may range from 10 to 30 joules. Consequently, the capacitor systems in existing ICD systems are all designed to store maximum energies of at least about 35 joules.

To solve for C knowing the desired stored energy E and the maximum charging voltage V, Eq. (4) can be rewritten as:

$$C = 2 * E/V^2 \qquad \text{Eq. (4)}$$

Using these two sets of equations together, it is possible to solve for the energy density D expressed in terms of the energy E per unit volume of the capacitor in terms of joules/cc as:

$$D = E/\text{Vol} \qquad \text{Eq. (5)}$$

where Vol is the total volume of the capacitor in cubic meters as defined by:

$$\text{Vol} = (A * t)/(\eta) \qquad \text{Eq. (6)}$$

where $\eta$ is the packaging efficiency expressed in terms of a percentage of volume storing energy per total volume of the capacitor. To express the volume calculated in Eq. (7) in cgs, rather than mks units, Vol must be multiplied by $10^6$. For a given desired stored energy E and charging voltage V, Eq. (5) and Eq. (6) are combined to give:

$$D = (\eta * E)/(A * t) \qquad \text{Eq. (7)}$$

Next, Eq. (1) is rewritten to solve for A as:

$$A = (C * t)/(K * \epsilon) \qquad \text{Eq. (8)}$$

into which Eq. (4) is substituted for C to yield:

$$A = (2 * E * t)/(V^2 * K * \epsilon) \qquad \text{Eq. (9)}$$

Substituting Eq. (9) into Eq. (7) provides a solution for the energy density D in terms of only the characteristics of the capacitor and the charging voltage V:

$$D = (\eta * K * \epsilon * V^2)/(2 * t^2) \qquad \text{Eq. (10)}$$

From Eq. (2), $F_m$ can be substituted for V/t to eliminate the charging voltage from Eq. (10) and solve for the energy density D solely in terms of the characteristics of the capacitor technology (K, ε, $F_m$, and η):

$$D = (\eta * K * \epsilon * F_m^2)/2 \qquad \text{Eq. (11)}$$

For a polyester thin film capacitor, for example, having a dielectric constant K of 3.25, a breakdown field strength $F_m$ of 800 V/μm, a thickness t of 8 μm, and a packaging efficiency η of about 50%, Eq. (11) predicts a theoretical energy density value of 9.2 joules/cc if the charging voltage equals or exceeds the minimum effective field voltage, which in this example equals 800 V/μm * 8 μm, or 6400 volts. This energy density is almost five times that of the aluminum oxide electrolytic capacitor technology of 1.77 joules/cc. Due to the nature of polymer films, the storage to volume ratio remains constant whether formed as a cylinder or as a flattened device. Thus, as compared to electrolytic capacitors which have an effective energy density of only about 1.33 joules/cc when packaged within the implantable housing of an ICD system, there is no packaging efficiency penalty for shaping the polymer thin film capacitors in a shape that is most convenient and efficient for packaging within the implantable housing of an ICD system.

The problem, however, is that Eq. (11) is valid for polymer film capacitors only so long as t is greater than about 10,000 nm and V is greater than the minimum effective field voltage necessary to generate the rated $F_m$ for that particular polymer film in order to allow the substitution from Eq. (2) into Eq. (10). In the case of the polyester thin film capacitor, V must be greater than 6400 volts in order to achieve the theoretical energy density value of 9.2 joules/cc. Such high voltages are simply impractical to achieve in ICD systems with present day microelectronic switching.

When the charging voltages are decreased below the minimum effective field voltage of a polymer film capacitor, it has been found that the breakdown field strength $F_m$ is effectively proportional to the dielectric thickness t. Thus, the maximum voltage $V_{max}$ that can be applied to a thin film capacitor of less than about 10,000 nm (instead of the relationship defined by Eq. (2)) proportional to the square of the dielectric thickness t:

$$V = Z * t^2 \qquad \text{Eq. (12)}$$

where Z is a constant derived from the breakdown field strength $F_m$ for the particular polymer thin film. Reworking Eq. (13) to solve for t yields:

$$t = (V/Z)^{0.5} \qquad \text{Eq. (13)}$$

Substituting Eq. (13) in Eq. (10) generates a solution for the energy density D in terms of only the characteristics of the capacitor technology (K, ε, Z and η) and the charging voltage V that is valid for polymer thin film capacitors having dielectric thicknesses t of between about 1,000 to 10,000 nm and charging voltages V greater than about 800 volts, but less than the minimum effective field voltage necessary to generate the rated $F_m$ for that particular polymer film. This equation is:

$$D = (\eta * K * \epsilon * V * Z)/2 \qquad \text{Eq. (14)}$$

Figure 6:
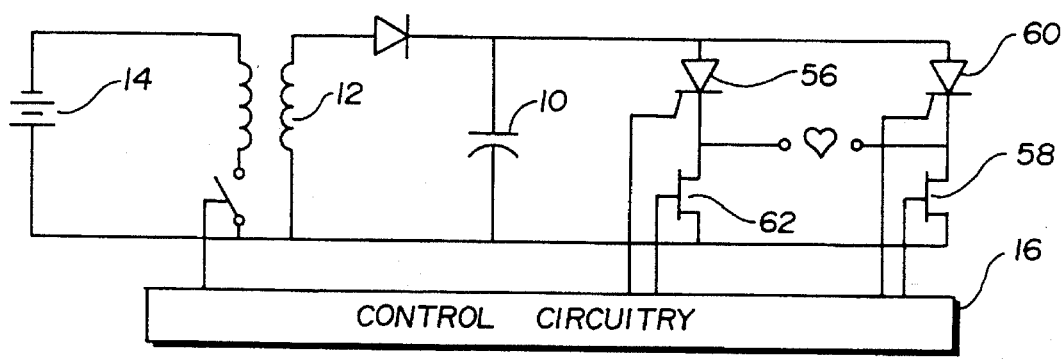
FIG. 6 is a simplified electrical schematic of an ICD system in accordance with a preferred embodiment of the present invention that employs a single polymer thin film capacitor and uses an H bridge output circuit to generate a biphasic waveform.

FIG. 6 represents a simplistic circuit depiction of a preferred embodiment of the present invention that employs a polymer thin film capacitor for the ICD system. As shown in FIG. 6, a single high voltage polymer thin film capacitor 10 is charged to an initial discharge voltage of at least 800 but less than about 1250 to 1500 volts by transformer 12 from battery source 14. Although only a single polymer thin film capacitor is shown in FIG. 6, it will be recognized that two or more polymer film capacitors could be utilized to provide an effective output capacitance in the ranges taught by the present invention. Above 1250 to 1500 volts, the peak output current of the discharge would be greater than about 25 to 30 amperes when discharged in the average myocardial resistance of 50 ohms. Consequently, for charging voltages above these values, the discharge output of the ICD system of the present invention must be handled using an alternative embodiment of the present invention as described below. Due to present voltage limitations of microelectronic switching circuitry, the maximum initial discharge voltage of the alternative embodiment is effectively limited to less than about 2000 volts.

Control circuitry 16 as shown in FIG. 6 responds to a sensing signal (not shown) to detect the presence of a cardiac arrhythmia, and, in response, selectively controls the charging and discharging of polymer thin film capacitor 10. In this embodiment, as in FIG. 4, a biphasic defibrillation countershock is initiated by closing SCR 56 and metal oxide semiconductor field effect transistor (MOSFET) 58. After a predetermined period of time of discharge across cardiac electrodes 38, MOSFET 58 is opened which starves the current through SCR 56 turning it off as well. The defibrillation countershock is completed by then closing SCR 60 and MOSFET 62 effectively reversing the polarity across cardiac electrodes 38. The countershock is truncated by opening MOSFET 62 which also in effect starves the current through SCR 60 allowing it to open as well. Because very little charge is left in the capacitor after the first phase, other techniques may be used for the second phase.

Figure 7:
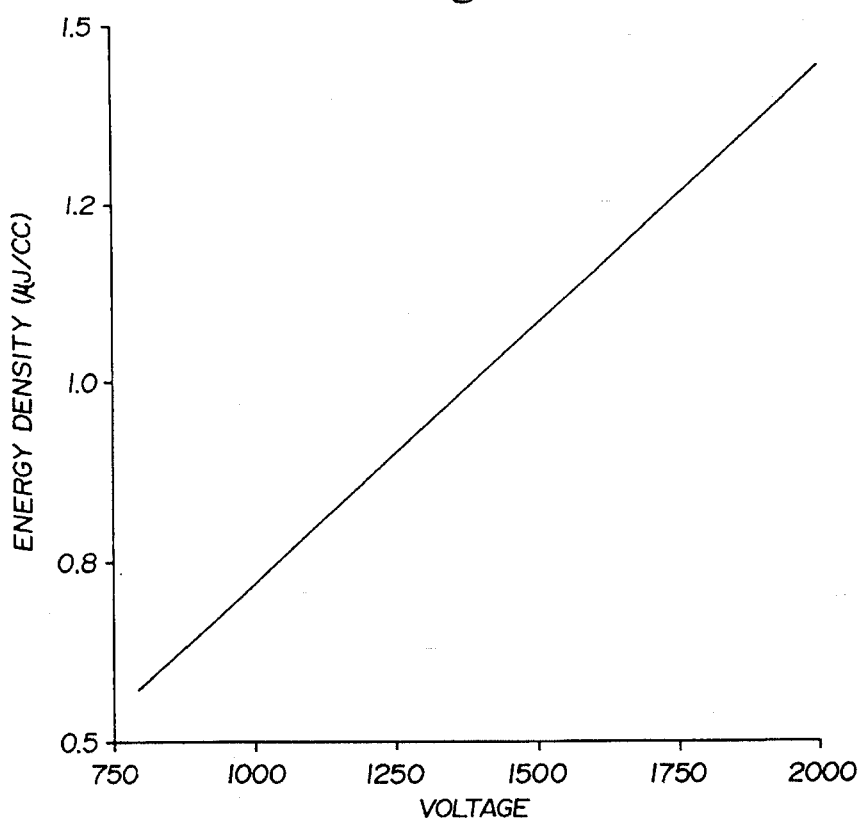
FIG. 7 is a graph depicting the energy density of a polyester thin film capacitor as a function of the discharge voltage between 800 and 2000 volts in accordance with the present invention.
Figure 8:
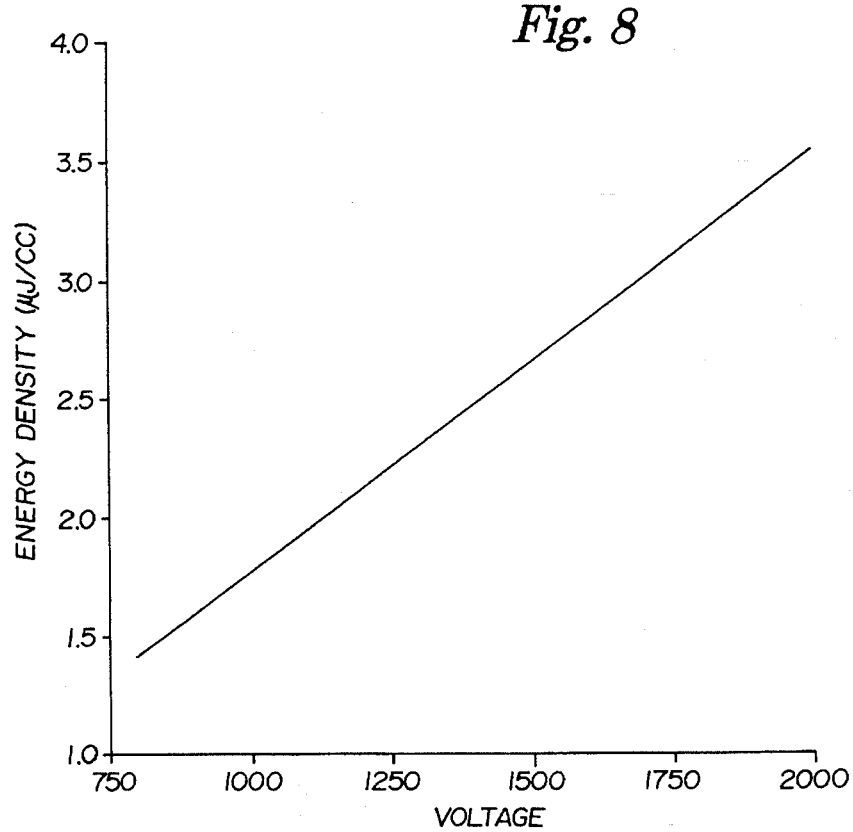
FIG. 8 is a graph depicting the energy density of a flouropolymer thin film capacitor as a function of the discharge voltage between 800 and 2000 volts in accordance with the present invention.

FIGS. 7 and 8 show a graph of the solution of Eq. (14) as a function of the initial discharge voltage V between 800 and 2000 volts for two different polymer thin film capacitors. In FIG. 7, a polyester thin film capacitor having a dielectric constant K of 3.25 and a field constant Z of 100 is shown. In FIG. 8, a flouropolymer thin film capacitor having a dielectric constant K of 8.0 and a field constant Z of 100 is shown.

The energy density of the flouropolymer thin film capacitor of FIG. 8 is representative of a polymer film with significantly improved mechanical strength and durability that is capable of being consistently rolled out to thinner dimensions. The flouropolymer thin film capacitor will have a capacitance of about 37 μF with a maximum rated charging voltage of about 1170 volts and a total volume of about 12.3 cc. The dielectric thickness of the flouropolymer thin film capacitor will be approximately 3.5 μm and will have an energy density of just over 2 joules/cc. The maximum stored energy will be 25.3 joules which can produce a delivered countershock having a duration of 3 milliseconds and a delivered energy of 24.3 joules, or 96% of the stored energy, with a final truncation voltage of about 230 volts. The leakage current at maximum voltage will be 100 μA and the capacitor will be hermetically sealed. The capacitor should be capable of at least 100 charging cycles, and preferably 200.

Figure 9:
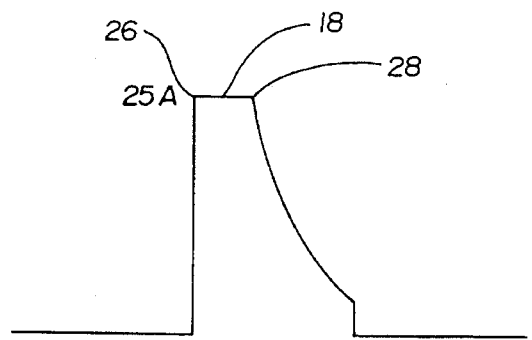
FIG. 9 is a graph depicting the current output of a current truncation embodiment of the ICD system of the present invention.
Figure 10:
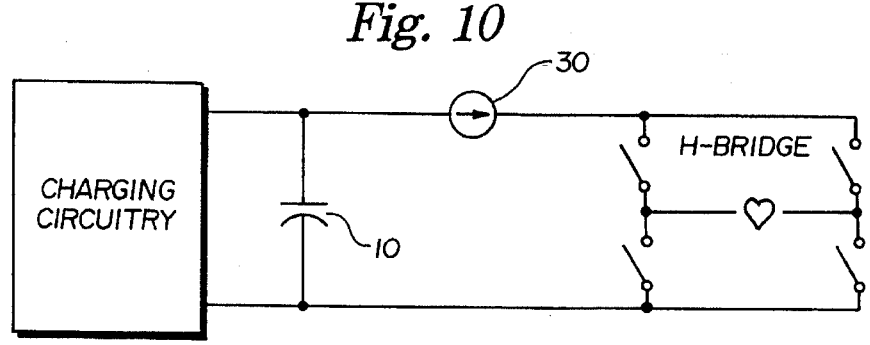
FIG. 10 is a simplified electrical schematic of an ICD system used to generate the current truncation embodiment of the ICD system of the present invention, the output of which is represented in FIG. 9.

An alternative embodiment of the present invention provides that the peak current generated by using discharge voltages in excess of those used by existing ICD systems will not cause damage to the myocardial tissue. To this end, if the discharge voltage exceeds about 1250 to 1500 volts, as shown for example at points 20 and 22, respectively, on FIGS. 7 and 8, the present invention can provide for non-linear current limiting circuitry to effectively limit the peak current to less than about 30 amperes, and preferably to less than about 25 amperes. Referring to FIG. 9, truncated countershock 24 has leading edge current 26 that has been truncated to a maximum of 25 amperes by non-linear output current truncater 30 as shown in FIG. 10. The current truncation embodiment of the present invention allows for versatility in choosing any truncation parameter, but 25 to 30 amperes may be considered the maximum allowable before significant tissue destruction is seen. During high peak current outputs, the current remains limited during time period 18 until polymer thin film capacitor 10 has discharged sufficiently to no longer sustain at 25 ampere output. At the end of time period 28, the output current begins to decay along the exponential curve typical for the particular capacitor 10. For a more detailed description of the various current truncaters 30 which can be used to accomplish this purpose, reference is made to the previously identified co-pending application entitled CURRENT TRUNCATED WAVEFORM DEFIBRILLATOR.

Figure 11:
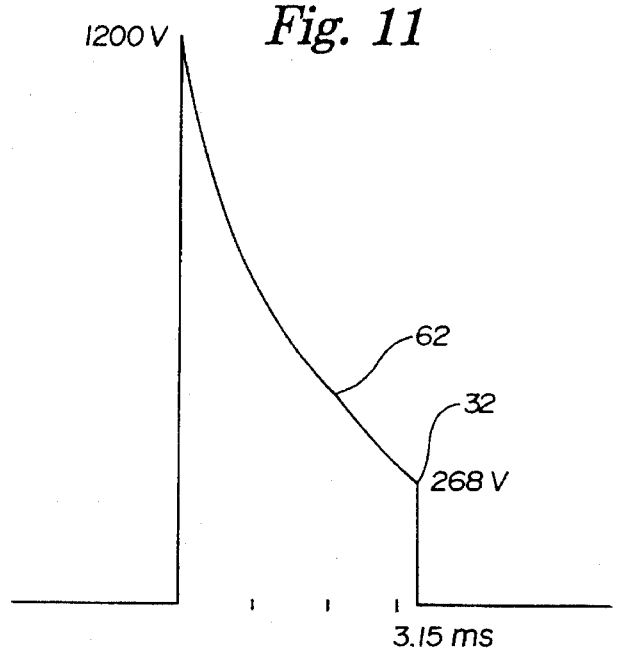
FIG. 11 is a graph depicting a voltage output for a specific polymer film capacitor of the circuit shown in FIG. 6.

FIG. 11 shows a voltage versus time discharge of an ICD system as shown in FIG. 6 that uses a 42 µF polymer film capacitor charged to 1,200 volts initially. Such a capacitor would store about a maximum stored energy of about 30 joules, and would have a time constant, τ, of about 2.1 millisecond, as defined by the equation:

$$\tau = R * C \qquad \text{Eq. (15)}$$

where R is the average myocardial tissue resistance of 50 ohms and C is the effective capacitance of the capacitor. If the capacitive-discharge countershock of this embodiment is truncated at one time constant at time point 62, as is the case in all existing ICD systems, the ICD system of the present invention would deliver a little more than 26 joules across the cardiac electrodes. The amount of energy delivered by such a system is sufficient to accomplish defibrillation, but the truncation of the discharge at one time constant is less than an optimum utilization of the energy. This less than optimum truncation because the duration of the discharge is significantly shorter than the average chronaxie value of the human heart. For a more detailed discussion of the relationship between the chronaxie value and the optimum capacitance and durations for electrical countershocks, reference is made to the previously identified co-pending application entitled IMPLANTABLE CARDIOVERTER DEFIBRILLATOR HAVING A SMALLER DISPLACEMENT VOLUME.

To avoid the detrimental effects of a discharge duration that is too short, the present invention provides that the discharge duration should be at least about equal to the average human chronaxie, or about 2.7 milliseconds based on the values established by current medical research. In the example shown in FIG. 11, if the capacitive-discharge is not truncated at one time constant point 62, but is instead truncated at a time point 32 equal to about 1.5 τ, or about 3.15 millisecond, the duration of the discharge is equal to or slightly greater than the average chronaxie value of the human heart. Possibly as important, the voltage at truncation point 32 in FIG. 11 is greater than about 260 volts, a value which is sufficiently large enough to avoid the detrimental effects of the low-voltage tail-end of the capacitive-discharge. The final voltage at truncation of a capacitive-discharge can be calculated based on the time constant, τ, and the duration d as follows:

$$V_f = V_i * e^{-d/\tau} \qquad \text{Eq. (16)}$$

where e is the natural logarithm value.

The avoidance of the detrimental effects of the low-voltage tail-end of the capacitive-discharge introduces another limitation on the capacitive-discharge of the present invention. It has been found that, on average, the voltage at the time of truncation cannot be lower than about 150 to 200 volts, and preferably should be higher than about 250 volts. Reworking Eq. (16) it is possible to solve for the lowest $V_i$ that can be used for a given capacitance in order to end up with a discharge duration of at least about 2.7 millisecond and a $V_f$ of at least 200 volts.

$$V_i = V_f e^{-d/\tau} \qquad \text{Eq. (17)}$$

Figure 12:
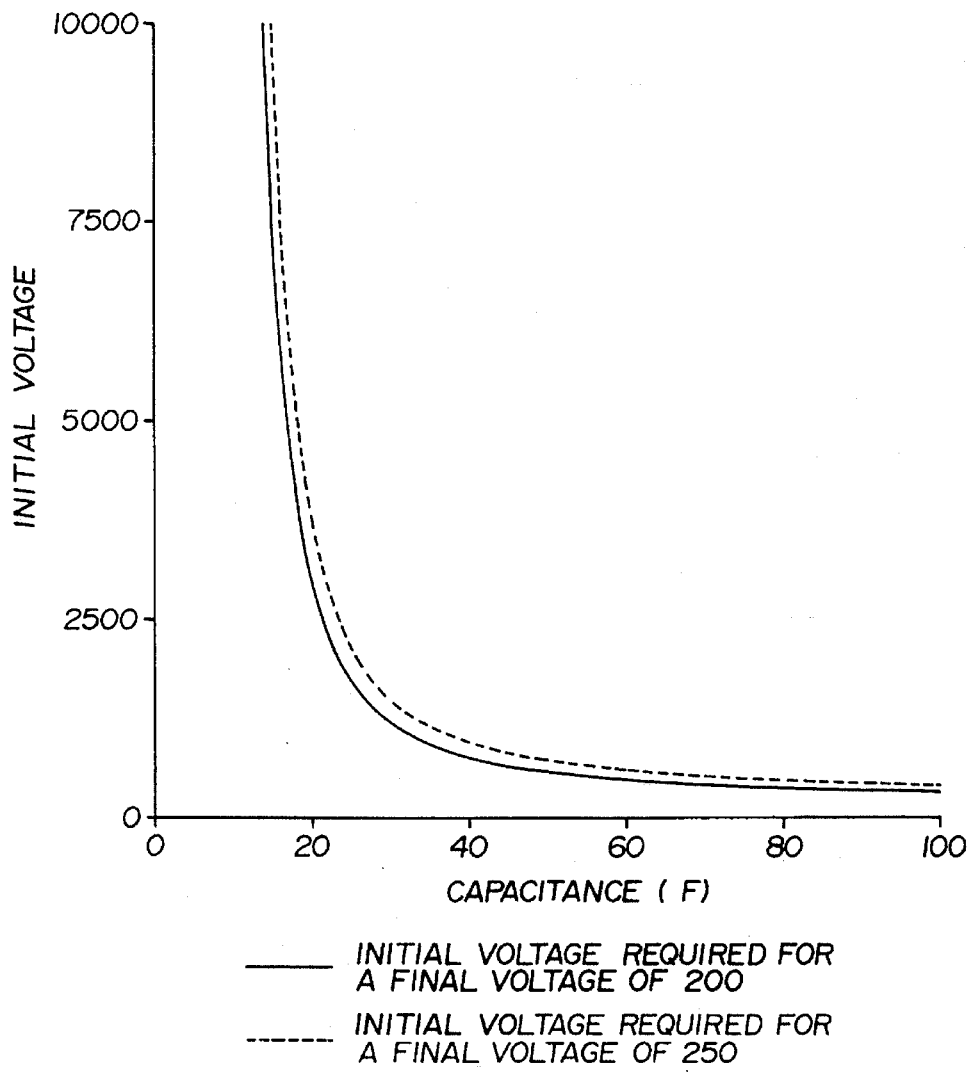
FIG. 12 is a graph depicting the relationship between capacitance and initial discharge voltage in order to obtain a final output voltage when the output is truncated of at least 200 or 250 volts.

FIG. 12 shows the minimum $V_i$ plotted as a function of capacitance C in accordance with Eq. (17) for $V_f = 200$ volts and for $V_f = 250$ volts. It can be seen from FIG. 12 that the effective capacitance of a polymer thin film capacitor must be greater than about 25 µF in order to have a workable initial charging voltage $V_i$ of less than about 2000 volts and a discharge duration such that the truncation voltage $V_f$ is greater than 200 to 250 volts.

In the alternative, the trailing voltage may be limited by the effective current theory which holds that the low trailing voltage is a problem only when it reduces the average current below the minimum current required by the cardiac strength-duration curve for a human patient. For a more detailed explanation of the relationship between the effective current and the cardiac strength-duration curve for a human patient, reference is made to the identified co-pending application entitled IMPLANTABLE CARDIOVERTER DEFIBRILLATOR HAVING A SMALLER DISPLACEMENT VOLUME. For a 25 µF capacitor, for example, the duration beyond which the average current starts to be reduced below the minium current required by the cardiac strength-duration curve is about 2.3 ms. For initial voltages of 1000, 1500 and 2000 volts, the value of the trailing voltage at the end of a 2.3 ms duration calculated by Eq. (16) will be 159, 238 and 318 volts, respectively.

Discharge duration can also be increased by increasing the time constant. As shown in Eq. (15), this can be achieved either by increasing resistance R or by increasing capacitance C. Increasing resistance introduces a lossy element which decreases efficiency. Increase capacitance can be accomplished by increasing the surface area of the capacitor, but this increases capacitor volume. Alternatively, one could decrease the dielectric thickness t, but, as previously discussed, the energy density of polymer films decreases as a function of the square of the dielectric thickness t. Another way is to increase the charge voltage, but this then forces thicker dielectrics which only serves to increase the capacitor volume. Consequently, another embodiment of the present invention uses as thin a dielectric as possible for a reasonable charge voltage and energy density and looks elsewhere to increase the countershock duration.

Figure 13:
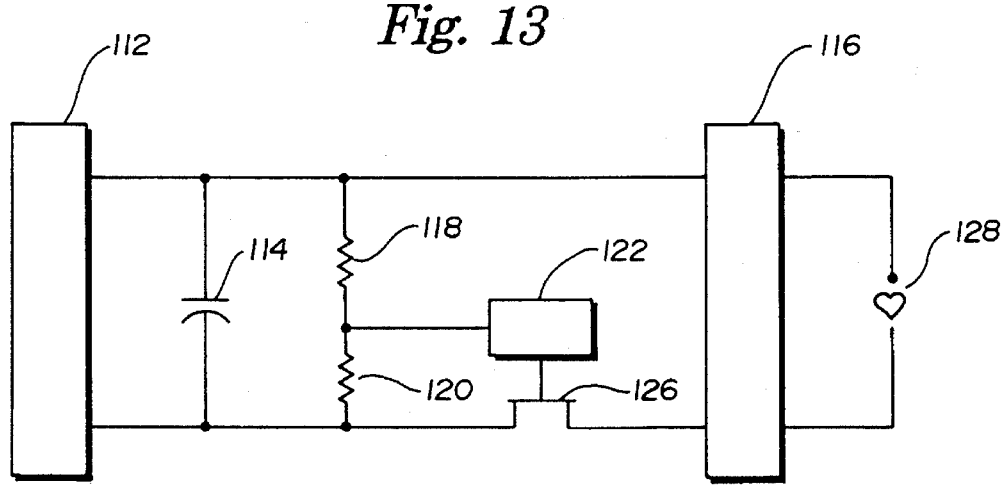
FIG. 13 is an electrical schematic diagram of an embodiment of the present invention which utilizes an extended duration technique.

In another embodiment of the present invention, the effective duration period is lengthened by rapid interruption of the discharge current across the cardiac electrodes. FIG. 13 depicts an embodiment of the present invention comprising a power source 112, a polymer film capacitor 114, a resistive divider comprised of a resistor 118 and a resistor 120 connected in parallel with capacitor 114, a discharge control means 116 for controlling the polarity of the discharge pulse to cardiac electrodes 128, a switch control means 122 electrically connected between resistor 118 and resistor 120 and an opposite end connected to the gate of a power FET switch 126 with source and drain connected in series between discharge control means 116 and capacitor 114. For a more detailed description of this embodiment, reference is made to the previously identified co-pending application entitled METHOD AND APPARATUS FOR

UTILIZING SHORT TAU CAPACITORS IN AN IMPLANTABLE CARDIOVERTER DEFIBRILLATOR.

In the embodiment depicted in FIG. 13, the ICD system utilizes switch control means 122 deriving its control based on the voltage perceived across resistors 118 and 120. This embodiment takes into account the voltage charge developed across the myocardial cell membrane and the electrode/serum interface which acts as a capacitance between the cardiac discharge electrodes which will be referred to in total as the cardiac capacitance.. The overall cardiac capacitance has a time constant of approximately 300μ seconds and so long as the interruption of the capacitive discharge is for periods less than about 300μ seconds, this cardiac capacitance serves as a filter to effectively smooth the discontinuous output of the ICD system. In the preferred version of this embodiment of the present invention, an asynchronous duration extension technique is used to greatly increase the efficiency of delivering the energy from a polymer film capacitor by delivering a wider pulse which more closely approximates a rectangular wave. In this embodiment, the invention as depicted in FIG. 13 utilizes a control means which is able to estimate the voltage effectively seen by the cell membranes by a simple estimation of the voltage across the discharge electrodes.

Figure 14:
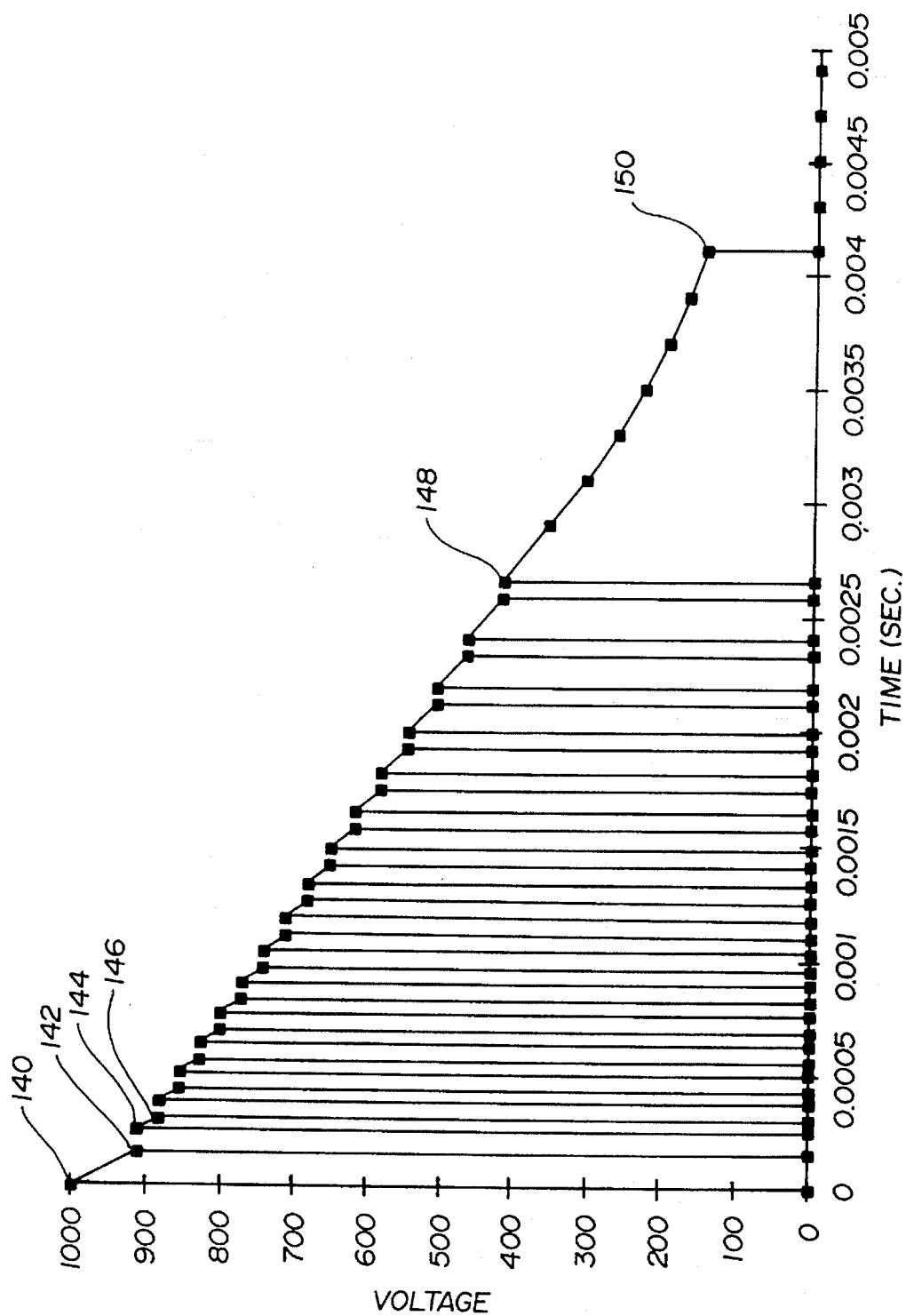
FIG. 14 is a graph depicting a voltage output for a specific polymer film capacitor of the circuit shown in FIG. 13.

FIG. 14 depicts a graphic representation of the output of the circuit disclosed in FIG. 13 for voltage versus time assuming no cardiac capacitance. In FIG. 14, a 34 μF polymer film capacitor is used, having been initially charged to only 1,000 volts. From time point 140 to time point 142 there is an exponential decay down to approximately 910 volts, at which time, switch control means 122 turns off switch 126. Between time point 142 and point 144 there is no discharge and as voltage drops to a preselected level as detected by switch control means at resistor dividers resistor 118 and resistor 120, switch control means can reactivate switch 126 showing the rise in voltage at point 144. The duration of discharge from time point 144 to time point 146 is considerably shorter than the discharge period from time point 140 to time point 142 because it takes considerably less time to take the electrode voltage from 300 back up to 400 than it did to take it from zero to 400 as it had to during the time period between time point 140 and time point 142.

As can be seen in FIG. 14 there is a more linear discharge between time point 146 and time point 148. At time point 148 the charge across capacitor 114 has fallen to 400 volts and can no longer maintain a 400 volt electrode potential and therefore switch control means will then cycle switch 126 on until terminal truncation at time point 150. From time point 148 to time point 150 there is exponential decay of capacitor 114. Thus, capacitor 114 has been discharged from 1,000 volts to just under 200 volts in just over 4 milliseconds instead of just under 2 milliseconds as would have happened if capacitor 114 had been allowed to discharge continuously. In this embodiment, by utilizing a variable duty cycle based on actual voltages, the present invention has achieved an output efficiently extending the discharge duration in such a way that the voltage as seen after the cardiac capacitance is not a rapidly decaying exponential, but more closely approaches the ideal rectangular waveform.

In the embodiment represented by the output curve of FIG. 14, a 34 μF polymer film capacitor charged to 1,000 volts will store 17 joules of energy. This capacitor will occupy 8.5 cc of volume and have a time constant of 1.7 milliseconds. The present invention through its various embodiments achieves a nearly rectangular discharge waveform using this small capacitor. A 34 μF polymer film capacitor can deliver 16.3 joules of energy through the myocardium while maintaining an average 7 amperes of current during the first phase lasting approximately 3.5 milliseconds. Thus, as embodied, a single 34 μF microfilm capacitor charged to only 1,000 volts is sufficient to generate an efficient defibrillation countershock pulse. In the embodiment represented by the output curve of FIG. 11, a 42 μF polymer film capacitor having a dielectric constant of about 8 will store 30 joules of energy in a 15 cc volume, deliver at least 26 joules as a countershock pulse in a monophasic or biphasic fashion and still occupy a smaller volume than present day ICD systems utilizing electrolytic capacitors.

We claim:

1. An implantable cardioverter defibrillator apparatus electrically connected to two or more implanted discharge electrodes located in a human patient for treating cardiac dysrhythmias, the apparatus comprising:

a) sensing means for sensing cardiac dysrhythmias;

b) charge storage means for storing an electric charge to be delivered to the two or more implanted electrodes, the charge storage means including one or more polymer thin film capacitors and having a maximum stored energy of less than about 35 joules when charged to a maximum charging voltage of at least about 800 volts;

c) power source means for charging the charge storage means; and d) discharge means for selectively discharging the charge storage means through the two or more implanted electrodes in response to the sensing of a cardiac dysrhythmia to deliver the electrical charge as a truncated capacitive-discharge electrical countershock that has a pulse duration greater than a defibrillation chronaxie duration of the human patient heart.

2. The apparatus of claim 1 wherein the one or more polymer film capacitors have an effective capacitance of less than about 80 μF and the maximum charging voltage is less than about 1500 volts.

3. The apparatus of claim 1 wherein the polymer thin film capacitor has a dielectric thickness of between about 1,000 nm and 10,000 nm.

4. The apparatus of claim 1 wherein the one or more polymer film capacitors have an effective capacitance of at least about 25 μF and the maximum charging voltage is less than about 2000 volts.

5. The apparatus of claim 4 wherein the electrical countershock is truncated at an output voltage of at least about 200 volts.

6. The apparatus of claim 4 wherein the electrical countershock is truncated at an effective current that is substantially at or above a minium current required by a cardiac strength-duration curve for the human patient.

7. The apparatus of claim 1 wherein the electrical countershock is discharged at a first polarity and the apparatus further comprises means for reversing an output voltage electrical countershock to an opposite polarity and continuing the discharge of the electrical countershock after the electrical countershock was discharged at the first polarity is truncated so as to produce a biphasic countershock with the pulse duration being defined by a duration of the electrical countershock at the first polarity.

8. The apparatus of claim 1 wherein the electrical countershock is limited to a maximum peak current of less than about 30 amperes.

9. The apparatus of claim 8 further comprising:

e) control means electrically connected between the discharge means and the discharge electrodes for limiting the peak current of the electrical countershock to less than about 30 amperes.

* * * * *